United States Patent
Guala (10) Patent No.: US 8,968,271 B2
(45) Date of Patent: Mar. 3, 2015

(54) CONNECTOR FOR MEDICAL LINES

(71) Applicant: Industrie Borla S.p.A., Moncalieri (Turin) (IT)

(72) Inventor: Gianni Guala, Turin (IT)

(73) Assignee: Industrie Borla S.p.A., Moncalieri (Torino) (IT)

( * ) Notice: Subject to any disclaimer, the term of this patent is extended or adjusted under 35 U.S.C. 154(b) by 36 days.

(21) Appl. No.: 13/739,586

(22) Filed: Jan. 11, 2013

(65) Prior Publication Data

US 2013/0187381 A1 Jul. 25, 2013

(30) Foreign Application Priority Data

Jan. 24, 2012 (IT) .............................. TO2012A0056

(51) Int. Cl.
*A61M 25/16* (2006.01)
*A61M 39/10* (2006.01)

(52) U.S. Cl.
CPC ........... *A61M 39/10* (2013.01); *A61M 39/1011* (2013.01); *A61M 2039/1033* (2013.01); *A61M 2039/1016* (2013.01); *Y10S 604/905* (2013.01)
USPC ............ 604/533; 604/534; 604/535; 604/905

(58) Field of Classification Search
CPC ............ A61M 39/10; A61M 39/1011; A61M 2039/1033; A61M 2039/1061; A61M 2039/0229
USPC ......... 285/133.4, 387.921; 403/7, 109.4, 118, 403/200; 604/240, 241, 399, 533
See application file for complete search history.

(56) References Cited

U.S. PATENT DOCUMENTS

| 4,432,759 A | * | 2/1984 | Gross et al. ................... 604/411 |
| 5,197,895 A | * | 3/1993 | Stupecky ..................... 439/194 |
| 5,403,840 A | * | 4/1995 | Vikmon et al. ............ 514/236.2 |
| 5,702,374 A | | 12/1997 | Johnson |
| 6,217,564 B1 | | 4/2001 | Peters et al. |

(Continued)

FOREIGN PATENT DOCUMENTS

EP 1 747 797 A1 1/2007
WO WO 2006/013433 A1 2/2006

(Continued)

OTHER PUBLICATIONS

Italian Search Report dated Nov. 20, 2012, for corresponding Italian Patent Application No. TO2010000056, filed on Jan. 24, 2012.

(Continued)

*Primary Examiner* — Nicholas Lucchesi
*Assistant Examiner* — Gerald Landry, II
(74) *Attorney, Agent, or Firm* — Heslin Rothenberg Farley & Mesiti P.C.; Victor A. Cardona, Esq.

(57) ABSTRACT

A connector for medical infusion lines, transfusion lines, and the like, includes a tubular body having at one end a male connector including an inner tubular element and an outer hollow element, which is internally threaded and can be coupled by screwing to a complementary female connector. The line connector further includes an outer maneuvering sleeve coupled in unidirectional rotation to the body in the direction corresponding to screwing of the male connector with respect to the complementary female connector and free to turn in the opposite direction, formed by two parts coupled together on the body of the connector.

8 Claims, 7 Drawing Sheets

(56) References Cited

U.S. PATENT DOCUMENTS

| | | | |
|---|---|---|---|
| 6,508,807 B1 * | 1/2003 | Peters | 604/533 |
| 7,731,708 B2 * | 6/2010 | Haarala et al. | 604/534 |
| 7,784,766 B2 | 8/2010 | Guala | |
| 8,048,038 B2 | 11/2011 | Guala | |
| 2003/0201639 A1 * | 10/2003 | Korkor | 285/81 |
| 2007/0088327 A1 * | 4/2007 | Guala | 604/533 |
| 2007/0129705 A1 * | 6/2007 | Trombley et al. | 604/523 |
| 2007/0129719 A1 * | 6/2007 | Kendale et al. | 606/41 |
| 2007/0218757 A1 * | 9/2007 | Guala | 439/589 |
| 2008/0172039 A1 | 7/2008 | Raines | |
| 2008/0190485 A1 | 8/2008 | Guala | |
| 2008/0287920 A1 * | 11/2008 | Fangrow et al. | 604/535 |
| 2009/0292274 A1 | 11/2009 | Guala | |
| 2010/0210990 A1 | 8/2010 | Lyons et al. | |
| 2011/0015580 A1 * | 1/2011 | Stroup | 604/207 |
| 2011/0044850 A1 * | 2/2011 | Solomon et al. | 422/28 |
| 2011/0196314 A1 * | 8/2011 | Smutney et al. | 604/247 |
| 2011/0224651 A1 * | 9/2011 | Ziman | 604/533 |

FOREIGN PATENT DOCUMENTS

| | | |
|---|---|---|
| WO | WO 2010/071812 A1 | 6/2010 |
| WO | WO 2012/002316 A1 | 1/2012 |

OTHER PUBLICATIONS

European Search Report completed Feb. 20, 2013, for corresponding EP Application No. EP 13 15 0798.

* cited by examiner

FIG. 13

CONNECTOR FOR MEDICAL LINES

CROSS REFERENCE TO RELATED APPLICATIONS

This application claims priority from Italian Patent Application No. TO2012A000056 filed on Jan. 24, 2012, the entire disclosure of which is incorporated herein by reference.

FIELD OF THE INVENTION

The present invention relates to connectors for medical lines, for example infusion lines and transfusion lines, of the type comprising a tubular body having at one end a male connector, for example of the luer-lock type or the like, including an inner tubular element and an outer hollow element, which is internally threaded and can be coupled by screwing to a complementary female connector.

STATE OF THE ART

In connectors of the type defined above, once the male connector is coupled and screwed to the complementary female connector there is the risk that the two connectors might come unscrewed and separate either accidentally or on account of a false manoeuvre, which evidently entails leakages of fluid and risks of even critical consequences for the patient to whom the connector is connected in use.

In an attempt to solve this problem it has been proposed in U.S. Pat. No. 5,702,374 to render the internally threaded outer hollow element of the male connector rotatable with respect to the inner tubular element, and to provide between them a toothed ring for mutual blocking in rotation.

If on the one hand this solution renders the line connector safer as regards any accidental unscrewing of the male connector from the female connector, for example due to yielding of the plastic material of which they are made or to phenomena of fatigue, it is altogether ineffective in the case of a wrong manoeuvre of voluntary unscrewing.

Document EP-1747797A1, filed in the name of the present applicant, describes a medical connector equipped with a dual unidirectional coupling associated to a female luer-lock connector, which operates in the direction of screwing with respect to a complementary male connector in a first axial position and in the opposite direction of unscrewing in a second axial position of the line connector. This unidirectional system is integrated in the line connector and requires, for passage from the first position to the second position, axial translation of the female connector with respect to a collar rigidly fixed to the body of the line connector, against the action of an elastic body, which is also integrated within the line connector.

From US-2008/172039 there is known a connector of the type defined above, corresponding to the preamble of Claim 1, i.e., one that moreover includes an outer maneuvering sleeve coupled in unidirectional rotation to a male luer-lock connector in the direction of screwing. Moreover the arrangement is such that once the male connector of the line connector has been screwed to the complementary female connector it can no longer be unscrewed, not even voluntarily. Installation of the sleeve on the body of the line connector is problematical and, in the installed condition, said sleeve is unstable both radially and axially.

SUMMARY OF THE INVENTION

The object of the present invention is thus to solve the aforesaid technical problem, and more in particular to render altogether safe the line connector in regard to any erroneous unscrewing of the male connector with respect to the complementary female connector, without the drawbacks referred to previously.

According to the invention, the above object is achieved thanks to the fact that the aforesaid outer maneuvering sleeve is free to turn in the opposite direction (i.e., in the direction of unscrewing of the line connector) and is formed by two parts coupled together on the body of the line connector.

Thanks to this arrangement, the maneuvering sleeve can be applied in a simple and precise way to the line connector, substantially without any undesirable radial or axial play, and ensures maximum safety against the risk of any accidental or erroneous unscrewing of the line connector.

Conveniently, the outer hollow element of the male connector has an outer ring gear, which co-operates with a ring of unidirectional pawling teeth provided inside the aforesaid outer sleeve.

The invention envisages two different embodiments, in the first of which the outer sleeve is formed by two axial portions coupled together, and in the second of which said sleeve includes two radial half-shells, which are also coupled together. In either case, coupling is preferably, albeit not necessarily, obtained via members of mutual snap-action coupling.

The tubular body of the line connector and the outer sleeve may moreover be mutually displaceable axially between a first position in which they are coupled together in unidirectional rotation in the direction of screwing of the male connector and a second position in which the outer sleeve is coupled in rotation with the body of the line connector in the direction corresponding to unscrewing of the male connector. This enables in use voluntary interruption of the line of flow between the line connector and the patient only if the operator is fully aware that he intends to unscrew the male connector from the female connector.

The invention finds particularly advantageous, but not exclusive, application in the case of valve connectors manufactured and marketed by the present applicant under the brand name "B-SITE®", which form the subject among other things of documents U.S. Pat. No. 7,784,766, U.S. Pat. No. 8,048,038 and US-2009/292274.

BRIEF DESCRIPTION OF THE DRAWINGS

The invention will now be described in detail with reference to the annexed drawings, which are provided purely by way of non-limiting example and in which.

DETAILED DESCRIPTION OF THE INVENTION

The two examples of embodiment of the invention that will be described hereinafter expressly refer to a valve connector for medical infusion lines, transfusion lines, and the like of the type corresponding to the ones described and illustrated in the patent documents referred to above filed in the name of the present applicant. It should, however, be noted that the invention is likewise applicable to any medical-line connector equipped with a male connector, typically of the luer-lock type or the like, that can be coupled to a complementary female connector of a conventional type, which is also of the luer-lock type or the like, which, as is well known to the person skilled in the branch, basically consists of a tubular element provided with an end external thread.

With initial reference to FIGS. 1 to 5, designated as a whole by 1 is a valve connector for medical lines comprising, in a way in itself known, for example from the already cited U.S. Pat. No. 8,048,038, a tubular body 2 made of moulded plastic material, set coaxially within which are a hollow pin 3 and an elastic sealing member 4 having a pre-slit elastic head 5 normally set in a closing condition within an inlet end 6 of the tubular body 2, formed by a female luer-lock connector. The hollow pin 3 forms at one end a closed terminal 7 facing the elastic head 5 and normally set at an axial distance therefrom, and at the opposite end a male luer-lock connector 8 constituted, in a way also in itself known, by an inner tubular element 9 with conical outer surface in communication with the hollow pin 3 and by an internally threaded outer hollow element 10. In use, the male luer-lock connector 8 is coupled by screwing to a complementary female luer-lock connector, and then an introducer of fluid is coupled to the inlet connector 6 so as to press the sealing member 4 axially against the action of a hollow elastic element 11 formed integrally therewith, towards the terminal 7 so as to get the pre-slit head 5 to assume an elastically deformed condition of opening and thus enable passage of fluid from the introducer to the male luer-lock connector 8.

According to the peculiar characteristic of the invention, the line connector further comprises an outer maneuvering sleeve, designated as a whole by 12, which is coupled in unidirectional rotation to the body 2 in the direction corresponding to screwing of the male luer-lock connector 8 to the complementary female luer-lock connector, and is free to turn in the opposite direction.

Figure 1:
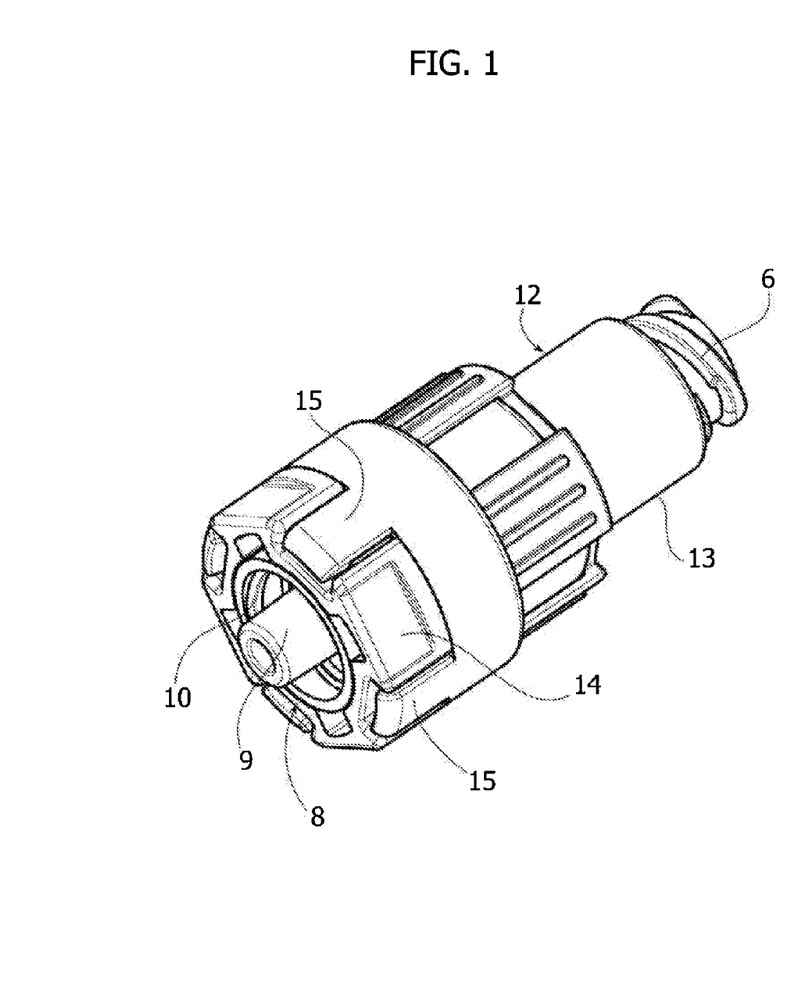
FIG. 1 is a schematic perspective view of a connector for medical lines according to a first embodiment of the invention.
Figure 2:
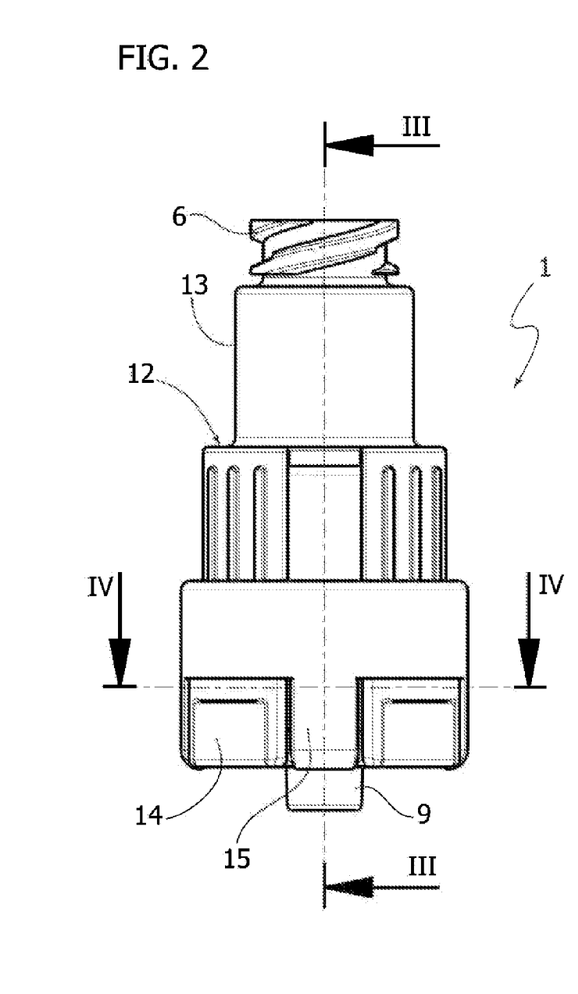
FIG. 2 is a view in elevation of the connector of FIG. 1.
Figure 3:
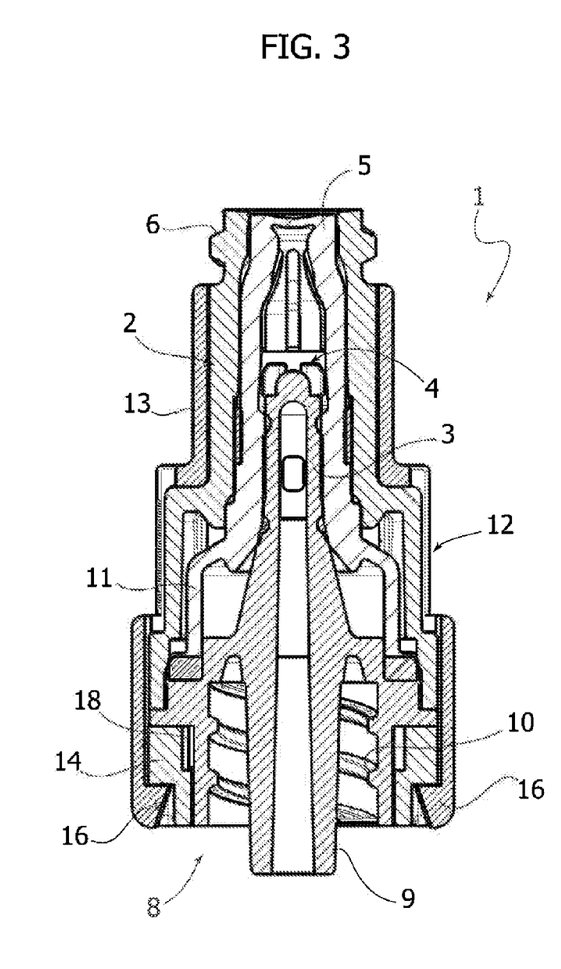
FIG. 3 is an axial sectional view according to the line III-III of FIG. 2.
Figure 4:
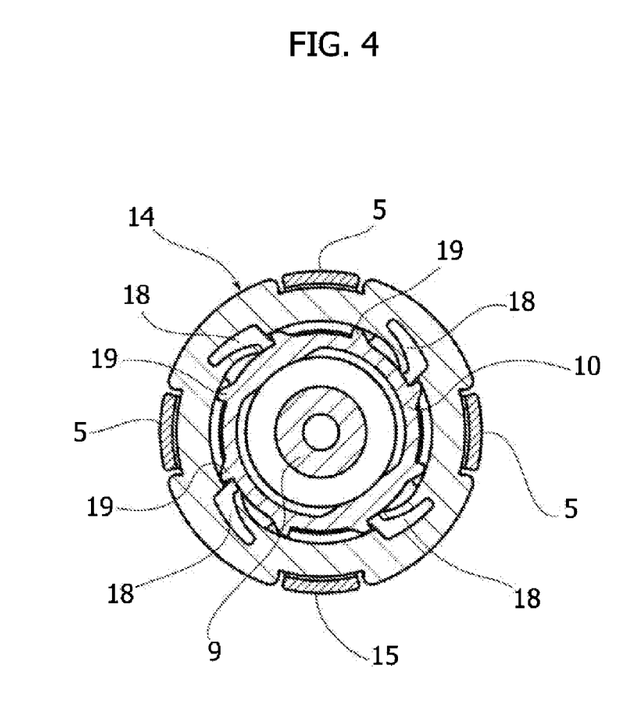
FIG. 4 is a cross-sectional view according to the line IV-IV of FIG. 2.
Figure 5:
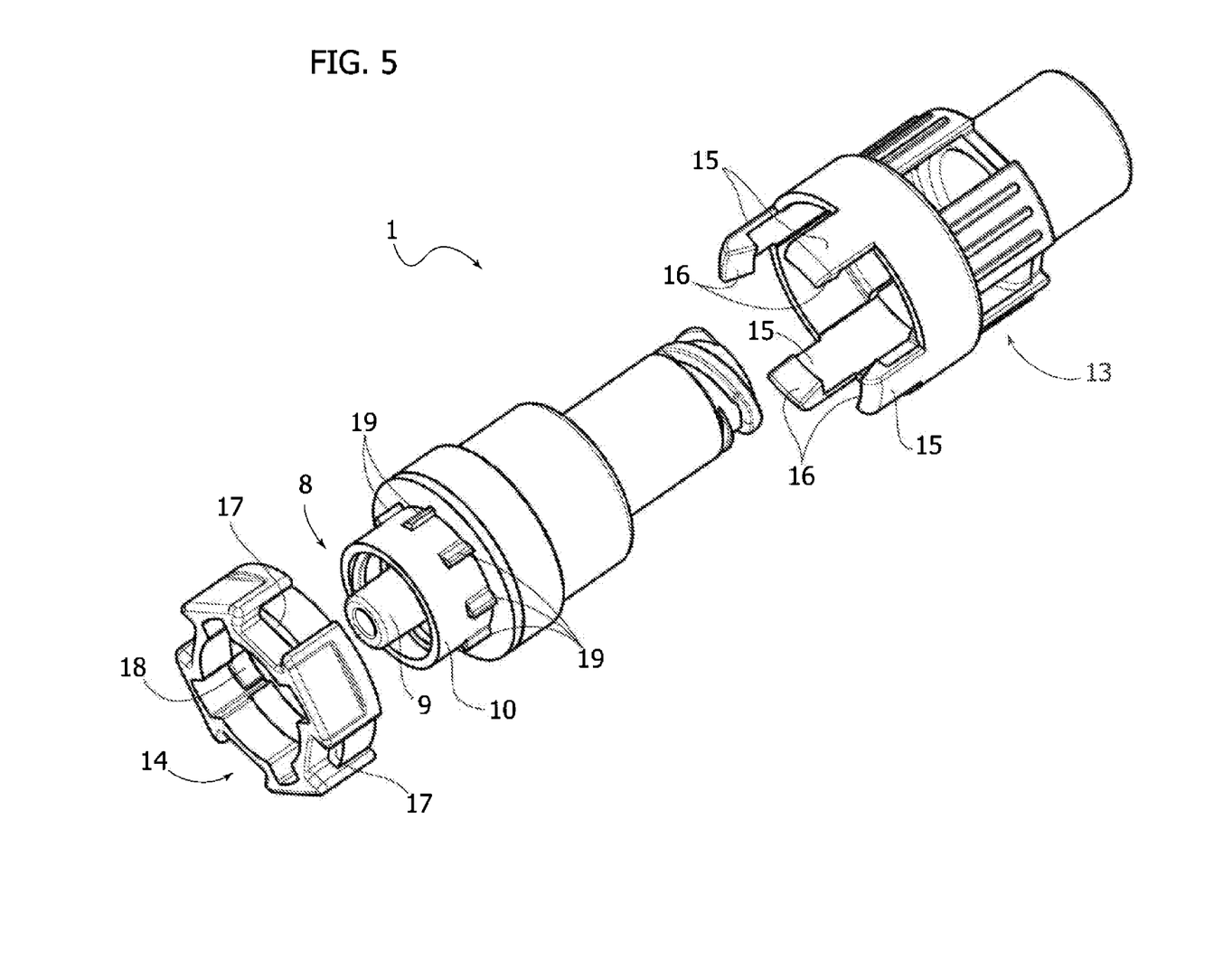
FIG. 5 is an exploded view at a larger scale the connector of FIG. 1.
Figure 6:
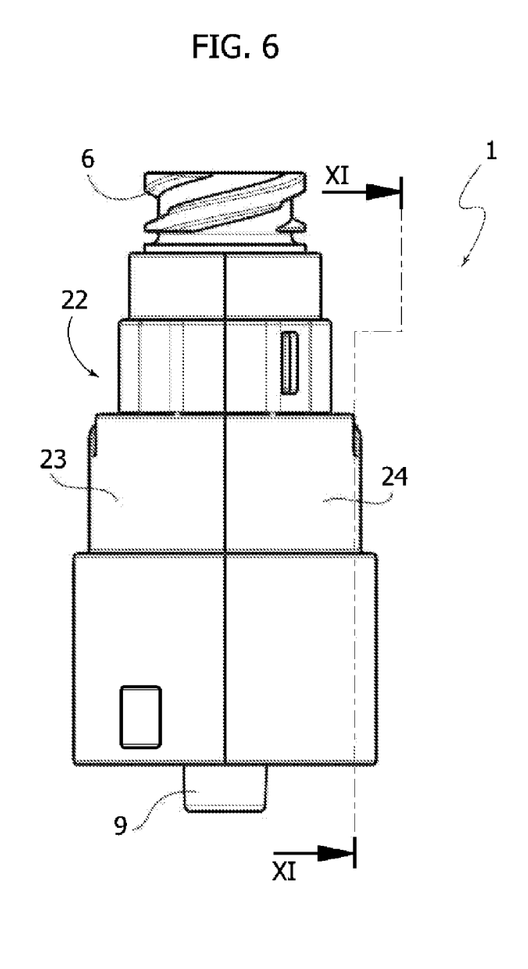
FIG. 6 is a front elevation of a second embodiment of the line connector according to the invention.
Figure 7:
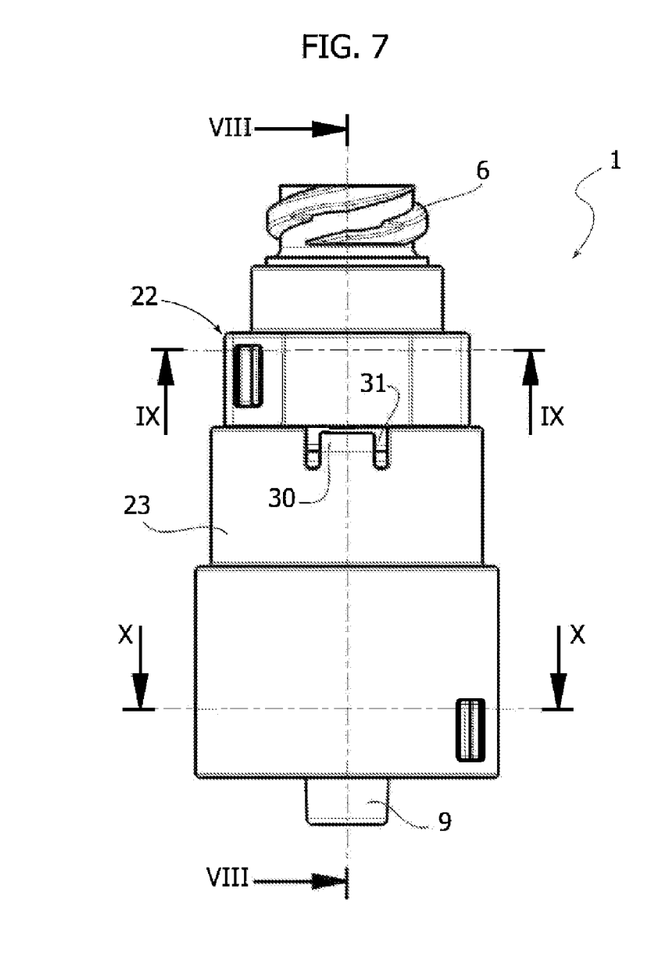
FIG. 7 is a side elevation of the line connector of FIG. 6.
Figure 8:
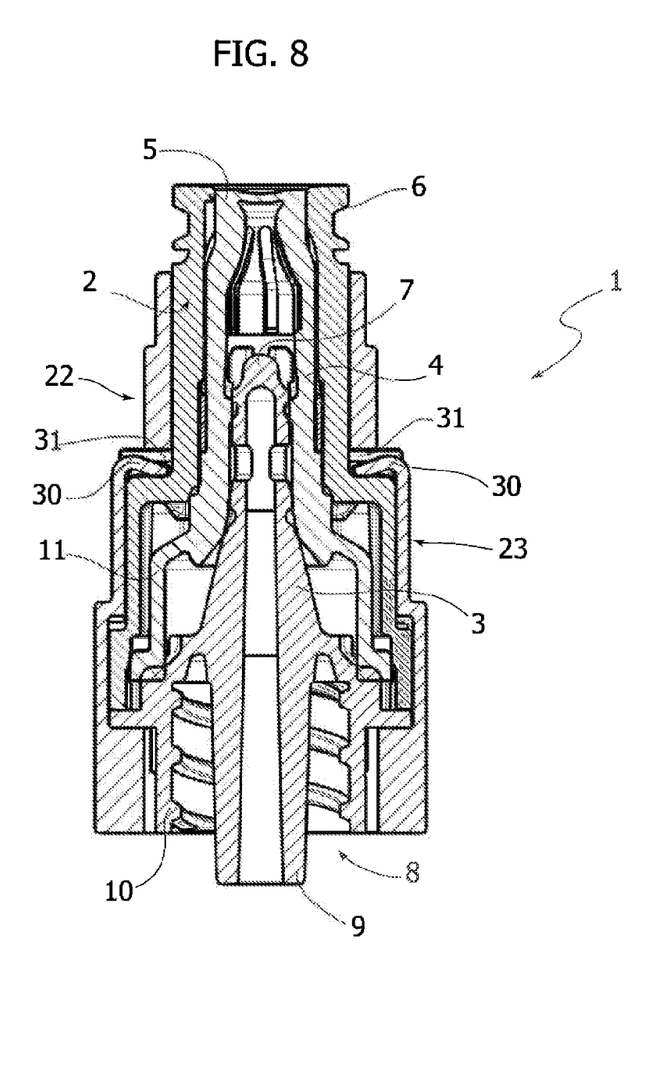
FIG. 8 is an axial sectional view according to the line VIII-VIII of FIG. 7.
Figure 9:
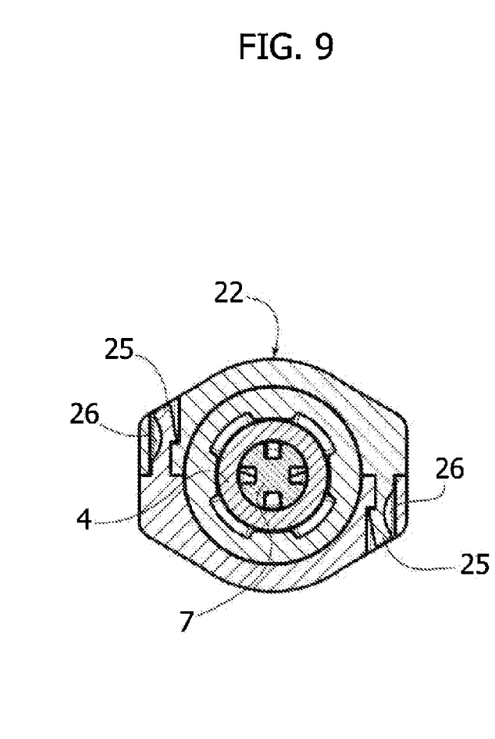
FIG. 9 is a cross-sectional view according to the line IX-IX of FIG. 7.
Figure 10:
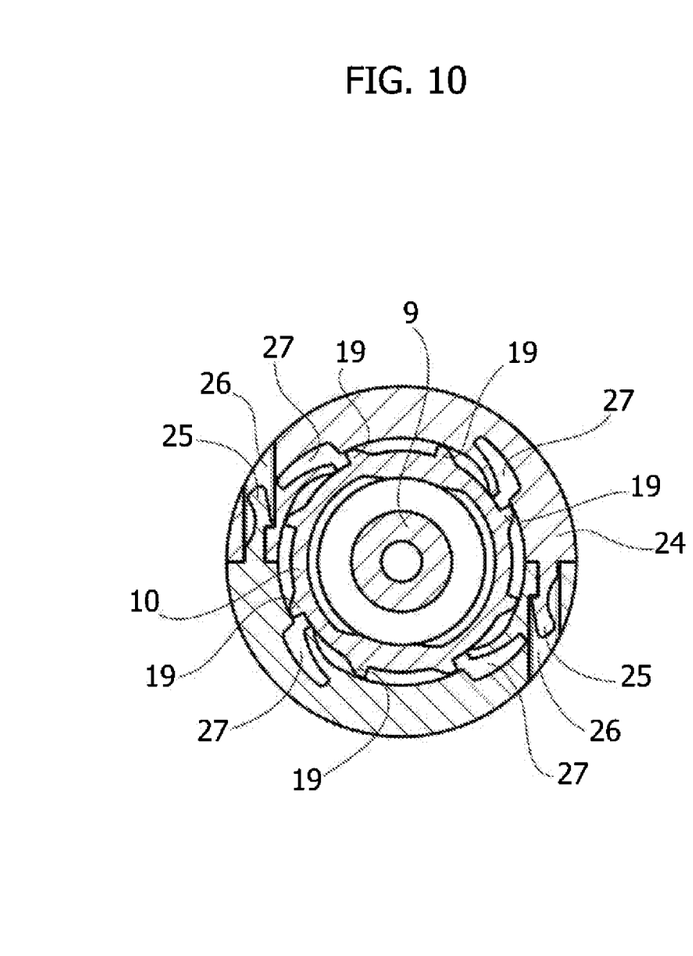
FIG. 10 is a cross-sectional view according to the line X-X of FIG. 7.
Figure 11:
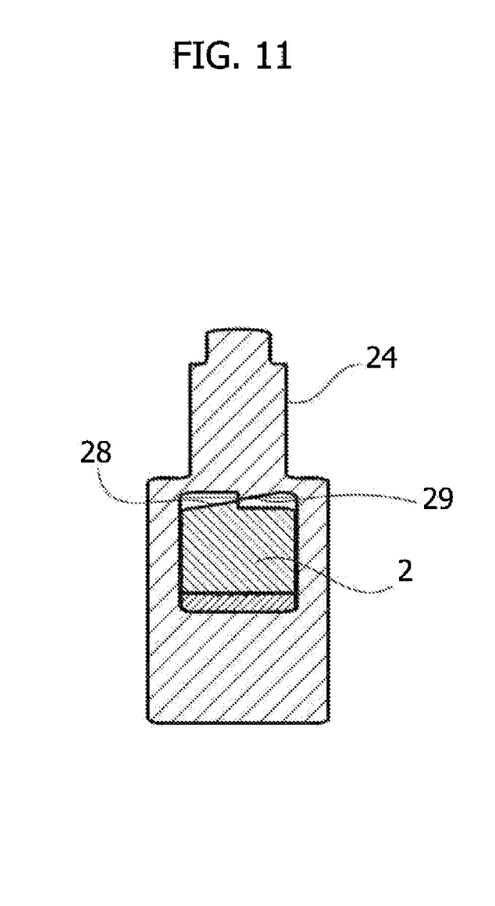
FIG. 11 is an axial sectional view according to the line XI-XI of FIG. 6.
Figure 12:
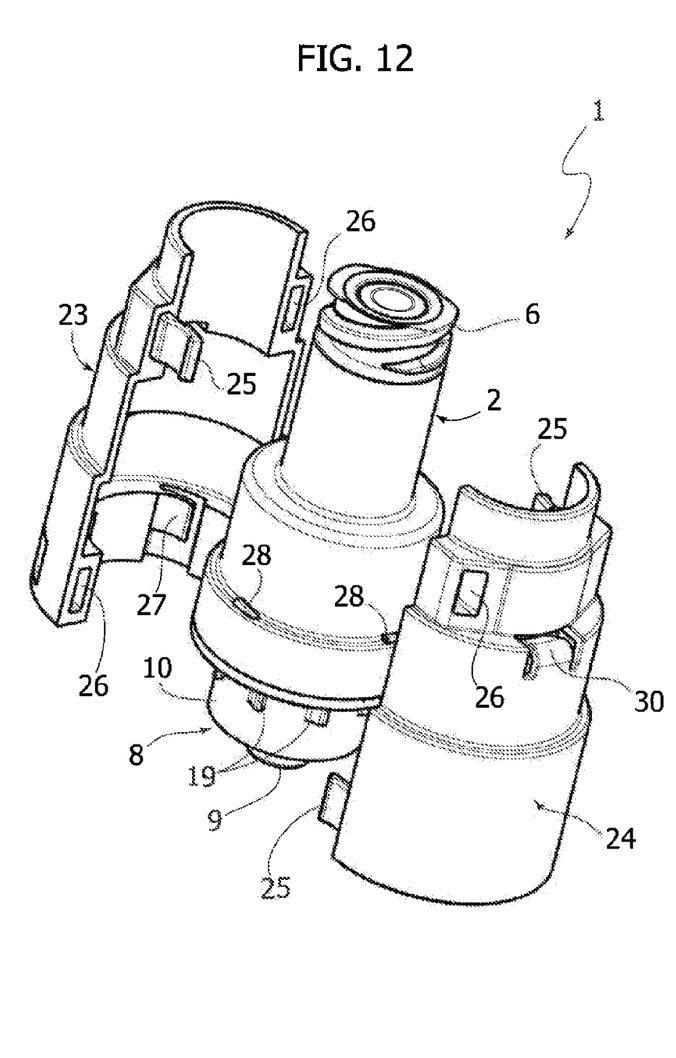
FIG. 12 is an exploded perspective view from above of the line connector FIG. 7.
Figure 13:
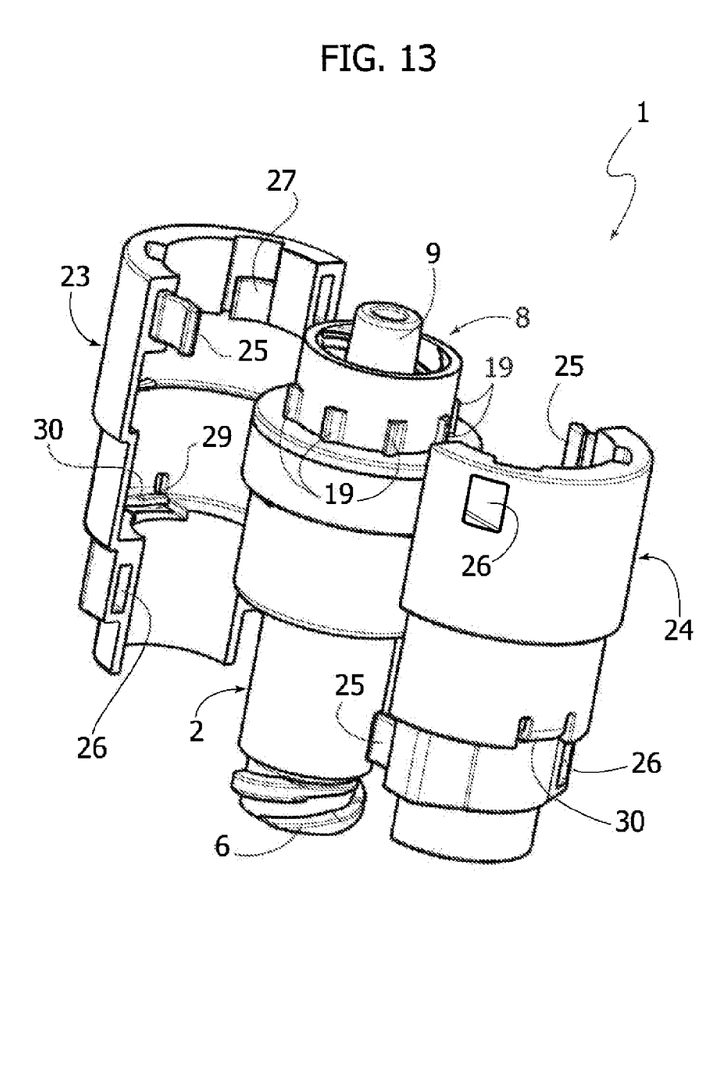
FIG. 13 is an exploded perspective view from beneath of the line connector FIG. 7.

The outer sleeve 12 extends axially, starting from the female luer-lock connector 6, until it covers entirely the outer hollow element 10 of the male luer-lock connector 8 and, in the case described herein with reference to FIGS. 1 and 5, it is formed by two axial portions 13, 14, which are also conveniently made of moulded plastic material. The axial portion 13 has a series of elastically sprung end legs 15 formed with respective engagement teeth 16, and the portion 14 consists of a ring that surrounds the outer hollow element 10 of the male luer-lock connector 8 and is formed externally with pawling parts 17 for snap-action engagement of the teeth 16 when the two parts 13, 14 are fitted axially in mutually opposite directions on the body 2.

The ring that constitutes the portion 14 is moreover formed internally with a ring of elastically sprung teeth 18 (more clearly visible in FIG. 4), with which a ring of teeth 19 formed on the outside of the hollow element 10 of the male luer-lock connector 8 co-operates. The arrangement of the teeth 18 and 19 is such that, as already explained previously, the outer sleeve 12 formed by the portions 13 and 14 is coupled in unidirectional rotation to the body 2 of the line connector only in the direction corresponding to screwing of the male luer-lock connector 8. In the opposite direction, the teeth 18 of the portion 14 jump elastically on the teeth 19 of the hollow element 10, thus enabling free rotation of the outer sleeve 12 with respect to the body 2 of the line connector 1. In this way, once the male luer-lock connector 8 is coupled by screwing to the complementary female luer-lock connector, it is prevented from unscrewing.

The variant illustrated in FIGS. 6 to 13, in which parts that are identical or similar to the ones already described previously are designated by the same reference numbers, differs from the first embodiment basically as regards two aspects: the outer maneuvering sleeve, designated as a whole by 22, is formed by two radial half-shells 23, 24 and is mounted on the body 2 of the line connector 1 in an axially slidable way between a first position, in which the sleeve 22 is coupled in unidirectional rotation to the body 2 of the line connector 1 in the direction corresponding to screwing of the male luer-lock connector 8 to the complementary female luer-lock connector, and a second position in which said sleeve 22 is coupled in rotation to the body 2 in the opposite direction, i.e., in the direction corresponding to unscrewing of the male luer-lock connector 9.

In detail, the two half-shells 23, 24 (which have an identical shape and can hence be obtained with a single die) also extend practically throughout the axial extension of the body 2 of the line connector starting from the female luer-lock connector 6 so as to gird at the bottom the entire outer hollow element 10 of the male luer-lock connector 8. The two half-shells 23, 24 are formed with respective sprung legs 25 designed to engage by snap action within corresponding openings 26 to form the sleeve 22, and each of them is moreover formed internally with respective elastically sprung teeth 27, altogether similar to the teeth 18 of the previous embodiment, which are designed to co-operate in the same way with the ring of external teeth 19 of the outer hollow element 10 of the male luer-lock connector 8. In other words, the teeth 27 couple the sleeve 22 torsionally to the body 2 of the line connector 1 in the direction corresponding to screwing of the luer-lock connector 8, whilst rotation of the sleeve 22 with respect to the body 2 is free in the opposite direction thanks to that the teeth 27 jump on the teeth 19.

As anticipated previously, the sleeve 22 is moreover displaceable axially with respect to the body 2 for a limited travel, starting from the position in which the teeth 27 are set axially in a position corresponding to the teeth 19, towards an unstable position in which engagement between the teeth 27 and the teeth 19 is no longer possible whilst the sleeve 22 couples torsionally to the body 2 of the line connector 1 in the direction corresponding to unscrewing of the male luer-lock connector 8 from the complementary female luer-lock connector. Said torsional coupling is implemented, in the second axial position, as a result of engagement between further rings of external teeth 28 and internal teeth 29, respectively, of the body 2 and of the half-shells 23, 24 of the sleeve 22. The teeth 28 and 29 are illustrated in greater detail in FIG. 11.

As has been said, the second position corresponding to engagement between the teeth 28 and 29 is unstable in so far as it is countered by a pair of elastically sprung appendages 30 formed integrally with the respective half-shells 23, 24 and engaged within corresponding recesses 31 of the body 2 of the line connector 1. When the sleeve 22 shifted in the second axial position is released, the sprung appendages 30 bring it back into the first position, thus obtaining disengagement between the teeth 28 and 29 and restoring engagement between the teeth 27 and 19.

As already pointed out previously, the invention is advantageously applicable not only to the valve connector 1 represented in the drawings but to any medical connector equipped with a male connector of the luer-lock type or similar types, which have a tubular element with conical outer surface that can engage with a female connector of a similar type (hence not necessarily a luer-lock connector). Obviously, also the other end of the line connector, i.e., the one opposite to the male connector, may be of any kind, for example formed by a simple duct applied even permanently to the body of the line connector.

Of course, the details of construction and the embodiments may vary widely with respect to what has been described and illustrated herein, without thereby departing from the scope of the present invention as defined in the ensuing claims.

In particular, the male connector of the line connector, instead of being of the luer-lock type, may be of any different type equipped with an inner tubular element with conical outer surface. Moreover, the union between the two axial portions 13, 14 or between the two radial half-shells 23, 24 may be obtained, instead of via snap-action couplings, with any different system, as likewise the elastic system that tends to keep the outer sleeve and the body of the line connector in the position of mutual unidirectional coupling in the direction of screwing may be different.

The invention claimed is:

1. A connector for medical infusion lines and transfusion lines, comprising:
    a tubular body having at one end a male connector including an inner tubular element and an outer hollow element, which is internally threaded and can be coupled by screwing to a complementary female connector;
    an outer maneuvering sleeve coupled in unidirectional rotation to the body of the connector in a first direction corresponding to screwing of said male connector with respect to said complementary female connector; and
    said outer maneuvering sleeve being free to turn in a second opposite direction relative to the first direction and formed by two parts coupled together on said body of the connector;
    said outer sleeve comprising two radial half-shells;
    said tubular body and said outer sleeve mutually displaceable axially between a first position and a second position, said tubular body and said outer sleeve coupled together in said first position in unidirectional rotation in said first direction of screwing of said male connector;
    said sleeve comprising elastically sprung appendages, said appendages tending to keep said outer sleeve and said body normally in said first position; and
    said body and said sleeve comprising coupling members coupling in rotation said sleeve and said tubular body in the second opposite direction corresponding to unscrewing of said male connector.

2. The connector according to claim 1, wherein said two parts are joined together via snap-fit coupling.

3. The connector according to claim 1, wherein said outer hollow element of the male connector has an outer ring gear, which co-operates with a ring of unidirectional pawling teeth provided inside said outer sleeve.

4. The connector according to claim 1, wherein said outer sleeve covers entirely the internally threaded outer hollow element of the male connector.

5. The connector according to claim 1, wherein the connector comprises a valve connector.

6. The connector according to claim 5, wherein said tubular body has, at the end opposite to said male connector, an inlet for insertion of an introducer of fluid and in that coaxially set within the cavity of the tubular body is a hollow pin having a closed terminal facing said inlet and axially set at a distance from the inlet, said hollow pin being in communication with said inner tubular element of the male connector; there being set between said tubular body and said hollow pin an intermediate sealing member including a pre-slit elastic head normally set in a condition of closing said inlet and displaceable axially towards said closed terminal of said hollow pin, as a result of insertion of said introducer of fluid within said inlet, to assume an elastically deformed condition of opening, and said sealing member moreover forming an elastic means tending to keep said head in said closing condition.

7. The connector according to claim 2, wherein said outer sleeve includes two axial portions.

8. The connector according to claim 2, wherein said outer sleeve includes two radial half-shells.

* * * * *